United States Patent
John et al.

(10) Patent No.: US 11,370,793 B2
(45) Date of Patent: *Jun. 28, 2022

(54) TRIAZOLOPYRIDINES AND TRIAZOLOPYRIMIDINES THAT LOWER STRESS-INDUCED P-TAU

(71) Applicant: NantNeuro, LLC, Culver City, CA (US)

(72) Inventors: Varghese John, Culver City, CA (US); Oleksandr Buzko, Culver City, CA (US); Dale Bredesen, Culver City, CA (US); Patricia Spilman, Culver City, CA (US); Barbara Jagodzinska, Culver City, CA (US)

(73) Assignee: NantNeuro, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/755,484

(22) PCT Filed: Aug. 29, 2016

(86) PCT No.: PCT/US2016/049270
§ 371 (c)(1),
(2) Date: Feb. 26, 2018

(87) PCT Pub. No.: WO2017/035528
PCT Pub. Date: Mar. 2, 2017

(65) Prior Publication Data
US 2019/0048012 A1 Feb. 14, 2019

Related U.S. Application Data

(60) Provisional application No. 62/210,947, filed on Aug. 27, 2015.

(51) Int. Cl.
C07D 487/04 (2006.01)
A61K 45/06 (2006.01)
A61K 31/519 (2006.01)
A61K 31/4439 (2006.01)
A61P 25/28 (2006.01)
C07D 471/04 (2006.01)

(52) U.S. Cl.
CPC ........ C07D 487/04 (2013.01); A61K 31/4439 (2013.01); A61K 31/519 (2013.01); A61K 45/06 (2013.01); A61P 25/28 (2018.01); C07D 471/04 (2013.01)

(58) Field of Classification Search
CPC .................................................. C07D 487/04
See application file for complete search history.

(56) References Cited

U.S. PATENT DOCUMENTS

| 6,342,503 B1 * | 1/2002 | Aldrich ................. A61K 31/44 514/272 |
| 6,448,261 B1 * | 9/2002 | Bakthavatchalam ... A61P 25/24 514/300 |
| 7,560,458 B2 | 7/2009 | Freyne et al. |
| 2015/0017148 A1 | 1/2015 | John et al. |

FOREIGN PATENT DOCUMENTS

| EP | 0778277 A1 | 6/1997 |
| WO | 1997-035539 A2 | 10/1997 |
| WO | 2013/082045 A1 | 6/2013 |
| WO | 2014-202541 A1 | 12/2014 |
| WO | 2017/035528 A1 | 3/2017 |

OTHER PUBLICATIONS

Chorvat et al. (J. Med. Chem.,1999, 42, 833-848).*
Kumar et al. Bioorganic & Medicinal Chemistry (2006), 14(12), 4029-4034.*
ISA/KR, International Search Report and Written Opinion, completed Dec. 12, 2016 for PCT Application No. PCT/US2016/049270, 14 pages.
Ye, Y. et al., "3D-QSAR study of corticotropin-releasing factor 1 antagonists and pharmacophore-based drug design", Neurochemistry International, Epub. Sep. 24, 2009.
Gannon, R. L. et al., "The corticotropin-releasing factor (CRF)1 receptor antagonists CP154,526 and DMP695 inhibit light-induced phase advances of hamster circadian activity rhythms", Brain Research, Epub. Mar. 21, 2006, vol. 1083, No. 1, pp. 96-102.
Chen et al., "Modulation of dendritic differentiation bycorti otropin-releasing factor in the developing hippocampus", PNAS, 2004, vol. 101, No. 44, pp. 15782-15787 (Cited from Specification).
International Preliminary Report on Patentability Chapter II received for PCT Application Serial No. PCT/US2016/049270 dated Dec. 19, 2017, 22 pages.

* cited by examiner

*Primary Examiner* — Brian E McDowell
(74) *Attorney, Agent, or Firm* — Martin Fessenmaier; Umberg Zipser LLP

(57) ABSTRACT

Pharmaceutical compounds, compositions, methods, and uses therefor are presented using selected triazolopyridines and triazolopyrimidines to inhibit or reduce phosphorylation of tau proteins or that act as antagonists of corticotropin-releasing factor. Viewed from another perspective, compounds, compositions, and methods are presented for treating or preventing symptoms of Alzheimer's disease by inhibiting or reducing the phosphorylation of tau proteins.

4 Claims, 15 Drawing Sheets

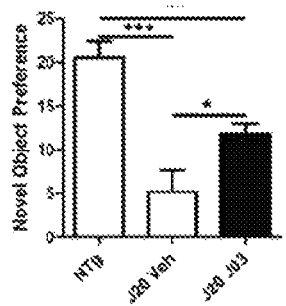
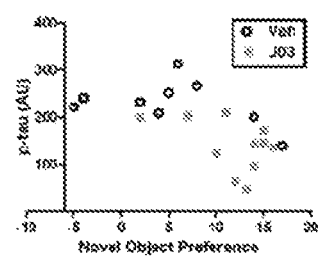
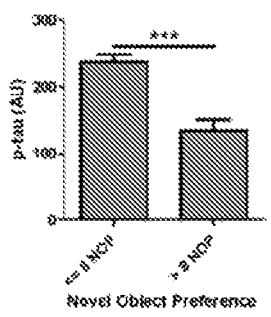
Figure 17A  Figure 17B  Figure 17C
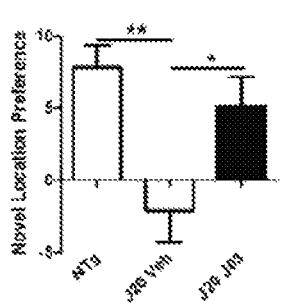
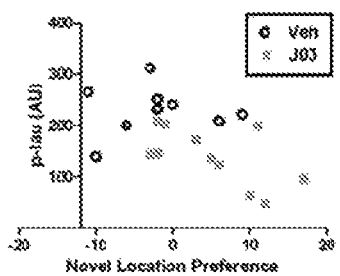
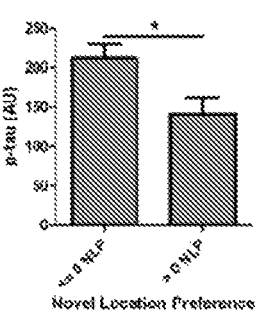
Figure 17D  Figure 17E  Figure 17F
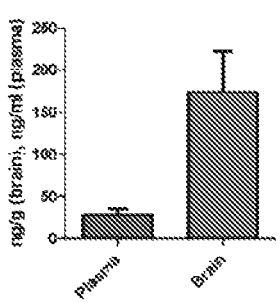
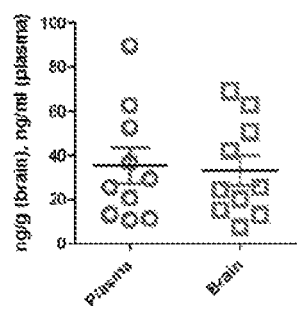
Figure 18A  Figure 18B
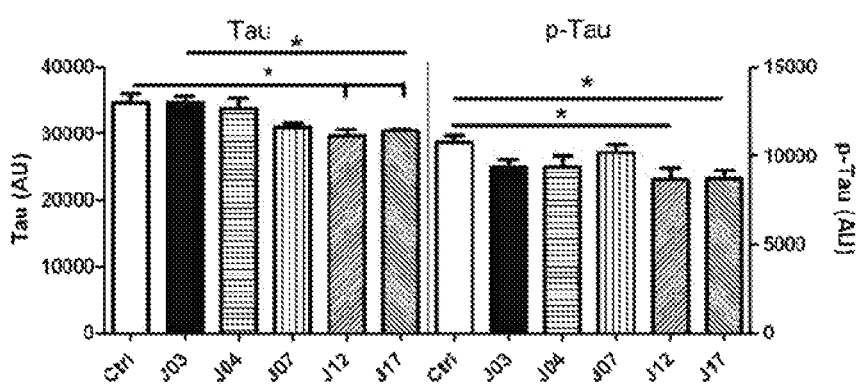
Figure 19

TRIAZOLOPYRIDINES AND TRIAZOLOPYRIMIDINES THAT LOWER STRESS-INDUCED P-TAU

This application claims the benefit of priority to U.S. provisional application having Ser. No. 62/210,947, filed on 27 Aug. 15.

FIELD OF THE INVENTION

The field of the invention is pharmaceutically active compounds, compositions, and methods therefor, and particularly as it relates to triazolopyridines and triazolopyrimidines.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications or patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Alzheimer's Disease (AD) is estimated to afflict more than 20 million people worldwide and is believed to be the most common cause of dementia. As the World population ages, the number of people with AD, currently approximately 5.4 million in the United States, will continue to rise. Alzheimer's is a neurodegenerative disease associated with progressive dementia and memory loss. Two key characteristics of AD are the accumulation of extracellular deposits containing aggregated Aβ peptide and neuronal synaptic loss in specific brain regions. Although AD pathogenesis is complex, compelling genetic and biochemical evidence suggest that overproduction of Aβ, or failure to clear this peptide is the earliest event in the amyloid cascade that leads to AD primarily through amyloid deposition, which is presumed to be involved in neurofibrillary tangle formation, neuronal dysfunction and microglia activation, that characterize AD-affected brain tissues.

Neurofibrillary tangles, along with plaques comprised of Aβ peptide, are a pathological hallmark of AD. Hyperphosphorylation of the microtubule-stabilizing protein tau leads to tangle formation. In people diagnosed with AD the level of tau phosphorylation has the closest correlation to cognitive impairment. Indeed, treatment regimes for AD including tau protein phosphorylation inhibitors are known (see e.g., US 2015/0017148, WO 2013/082045), as are treatments to reduce tau protein phosphorylation by use of triazolopyrimidines derivatives to inhibit glycogen synthase kinase 3 (see e.g., U.S. Pat. No. 7,560,458).

However, all known treatments fail to appreciate the benefits of particular triazolopyrimidine derivatives when used as corticotropin-releasing factor ("CRF-1") antagonists to reduce or prevent p-tau production. Therefore, there is still a need for new and alternative treatments for AD with via a CRF-1 antagonist pathway.

SUMMARY OF THE INVENTION

The inventive subject matter is directed to pharmaceutical compounds, compositions, and methods therefor, and particularly to selected triazolopyridines and triazolopyrimidines that inhibit or reduce phosphorylation of tau protein (phospho-tau or p-tau) or that act as antagonists of corticotropin-releasing factor. Viewed from another perspective, the inventive subject matter is drawn to compounds, compositions, and methods for treating or preventing symptoms of Alzheimer's disease by inhibiting or reducing the production of p-tau.

In one aspect of the inventive subject matter, the inventors contemplate a compound having a structure according to Formula I

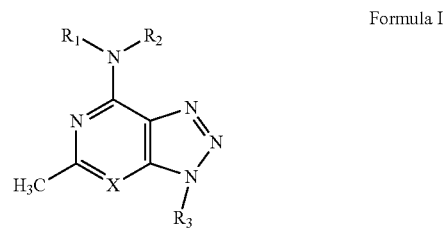

Formula I wherein X is CH, or more preferably N. $R_1$ and $R_3$ independently from each other can be aryl (substituted or non-substituted), a heteroaryl (substituted or non-substituted), an alkyl (substituted or non-substituted), a cycloalkyl (substituted or non-substituted), a heterocycloalkyl (substituted or non-substituted), a heteroalkyl (substituted or non-substituted), or an alkoxy(substituted or non-substituted). It is further contemplated that $R_2$ can be, deuterium, $CF_3$, $CHF_2$, or $CH_2F$, and is most preferably hydrogen or $CH_3$.

Therefore, and viewed form a different perspective, compounds are also contemplated such that $R_1$ and $R_3$ independently have a structure selected from

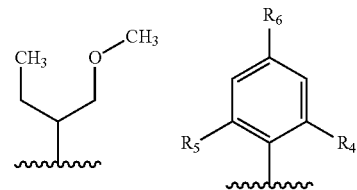

where each of $R_4$, $R_5$, and $R_6$ can be one of hydrogen, deuterium, OH, a halogen, a methyl, $CF_3$, $CHF_2$, $CH_2F$, or an alkoxy. In preferred aspects, the compounds will have a structure such that $R_1$ and $R_3$ independently have a structure selected from

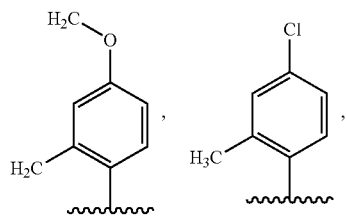

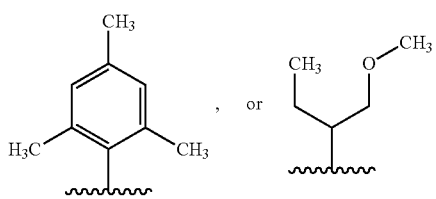, or
Most preferably, compounds of the inventive subject matter will have a structure according to any one of Formulae II-VIII:
Formula (II)
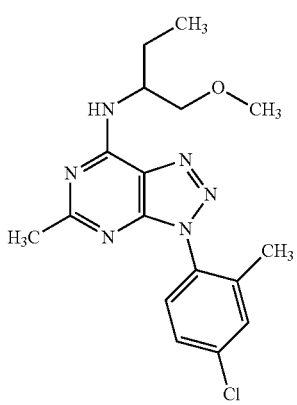
Formula (III)
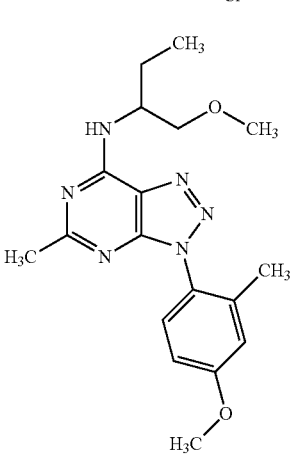
Formula (IV)
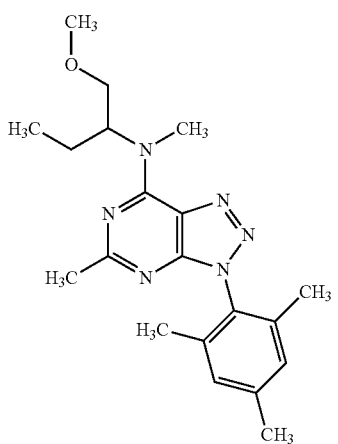
Formula (V)
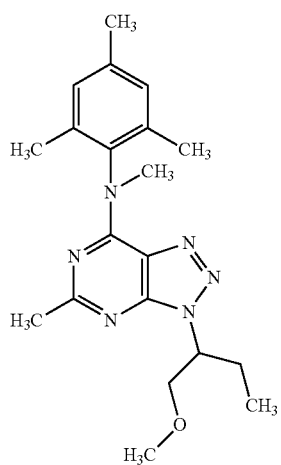
Formula (VI)
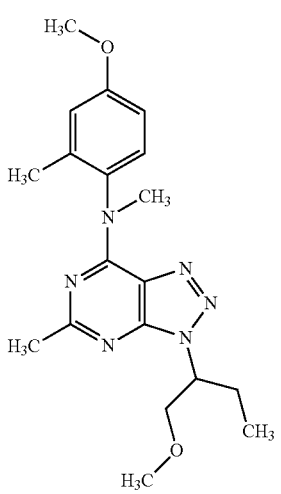
Formula (VII)
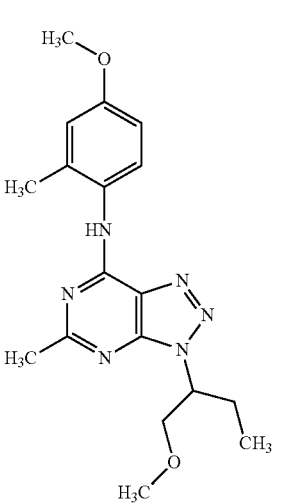

-continued

Formula (VIII)

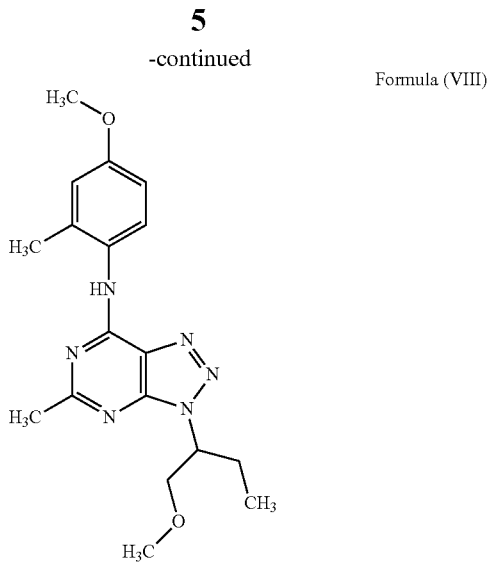

In further contemplated aspects pharmaceutical compositions are contemplated that comprise a pharmaceutically acceptable carrier in combination with one or more compound presented herein, wherein the compound may be present as a pharmaceutically acceptable salt, a hydrate, a solvate, or in crystalline form. Most preferably, the compound will be present in the pharmaceutical composition in an amount effective to inhibit or reduce production of p-tau, or as an antagonist of CRF-1 in a patient when administered (e.g., orally or via injection) to the patient. As will be readily appreciated, such formulations have CRF-1 inhibitory activity and will be suitable (alone or in combination with another pharmaceutical agent) for treatment of a neurological condition, and particularly for treatment of Alzheimer's Disease.

Therefore, the inventors also contemplate the use of one or more compounds presented herein in the manufacture of a pharmaceutical composition or medicament, especially where the composition is used in the treatment of a neurodegenerative disease, and/or where the composition is for the reduction of CRF-1 activity or p-tau levels in a patient. Viewed from another perspective, use of compositions of triazolopyrimidines and triazolopyridines to reduce or prevent neurofibrillary tangling are contemplated. Consequently, CRF-1 inhibitors, triazolopyridines, and triazolopyrimidines, and uses thereof, are also specifically contemplated herein and particularly include treatment of neurological conditions (e.g., Alzheimer's Disease). The inventors also contemplate methods for treating and/or preventing neurological conditions that typically comprise a step of administering to a patient an effective amount of one or more compounds presented herein.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIGS. 17A-17F reflect experimental results for further studies with J03.
FIGS. 18A-18B reflect experimental results for further studies with J03 with respect to pharmacokinetics.
FIG. 19 reflects experimental results for J03 analogs.

DETAILED DESCRIPTION

Figure 1:
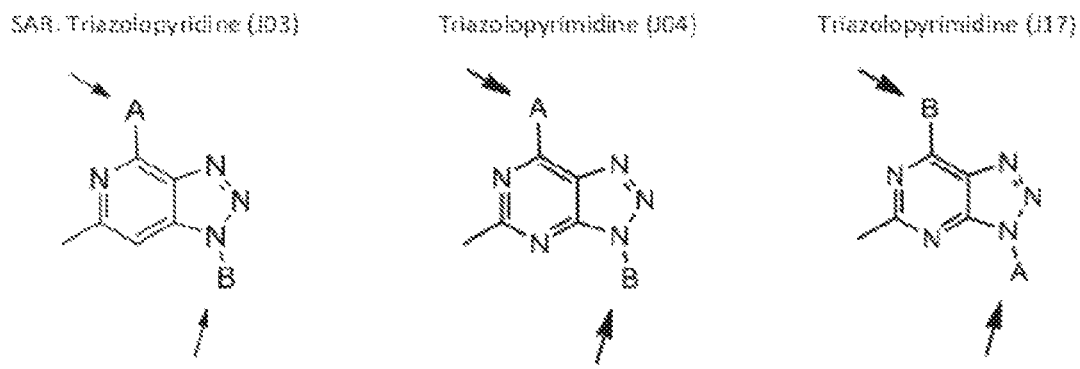
FIG. 1 illustrates design considerations for J03 analogs.

The inventive subject matter is directed towards various pharmaceutical compounds, compositions, and methods therefor, and particularly to selected triazolopyridines and triazolopyrimidines that inhibit or reduce phosphorylation of tau protein (phospho-tau or p-tau) or that act as antagonists of corticotropin-releasing factor, for example in the treatment or prevention of AD symptoms. So prepared compounds, compositions and methods are deemed to be useful in the manufacture of a medicament and the treatment of neurodegenerative diseases responsive to such compounds and compositions. While not wishing to be bound by any particular theory or hypothesis, it is contemplated that the compounds will reduce or inhibit phosphorylation of tau proteins via a CRF-1 antagonist pathway, thus reducing or preventing neurofibrillary tangling. Consequently, such compounds may be particularly beneficial for treatment of ongoing AD, in the delay or prevention of the onset of AD, in the onset of mild cognitive impairment ("MCI"), in the delay of a transition from MCI to AD, and in the delay or prevention of MCI.

In especially preferred aspects of the inventive subject matter, several compounds were identified and further evaluated for reduction or prevention of tau protein phosphorylation.

Contemplated Compounds

The present inventive subject matter is related to compounds having general Formula (I) or a pharmaceutically acceptable salt thereof, wherein

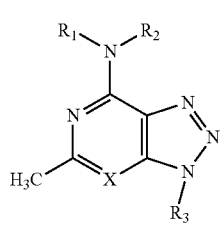

Formula I wherein X is a CH or heteroatom, preferably N. $R_1$ and $R_3$ are independently an aryl, substituted aryl, heteroaryl, substituted heteroaryl, alkyl, substituted alkyl, cycloalkyl, substituted cycloalkyl, heterocycloalkyl, substituted heterocycloalkyl, heteroalkyl, substituted heteroalkyl, alkoxy, or substituted alkoxy; and $R_2$ is $CH_3$, $CF_3$, $CHF_2$, $CH_2F$, or a heteroatom, preferably hydrogen or deuterium.

Another embodiment provides a compound of Formula I or a pharmaceutically acceptable salt thereof such that $R_1$ and $R_3$ independently have a structure selected from

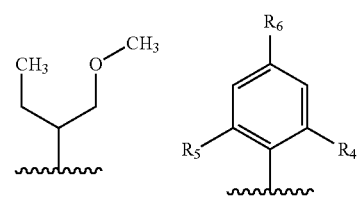

where each of $R_4$, $R_5$, and $R_6$ can be one of a heteroatom, preferably hydrogen or deuterium, a halogen, preferably Cl, OH, an alkyl (optionally substituted), preferably methyl, $CF_3$, $CHF_2$, $CH_2F$, or a heteroalkyl (optionally substituted), preferably an alkoxy.

Still further embodiments provide compounds of Formula I or a pharmaceutically acceptable salt thereof such that $R_1$ and $R_3$ independently have a structure selected from

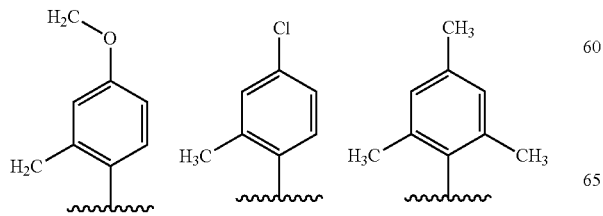

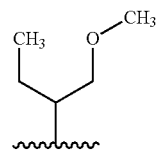

Yet further embodiments provide compounds according to Formula I, or a pharmaceutically acceptable salt thereof, such that $R_2$ is hydrogen. In some embodiments having compounds of Formula I where $R_2$ is hydrogen, $R_1$ is one of

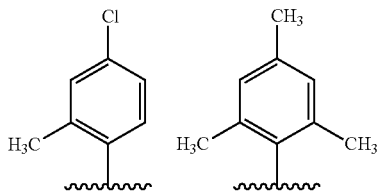

and preferably

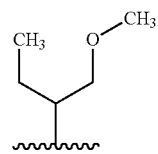

and most preferably

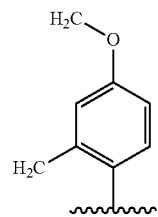 [SMILES: *c1ccc(OC)cc1C]

In such embodiments, $R_3$ can be

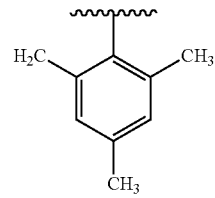

and preferably one of

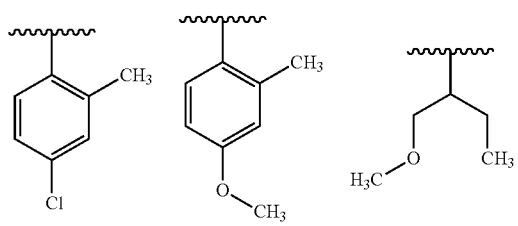 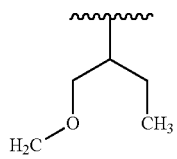

Yet further embodiments provide compounds according to Formula I, or a pharmaceutically acceptable salt thereof, such that $R_2$ is $CH_3$. In some embodiments having compounds of Formula I where $R_2$ is $CH_3$, $R_1$ is

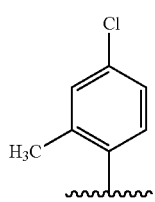

and preferably

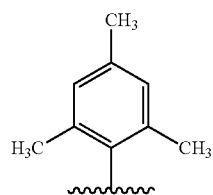

and most preferably one of

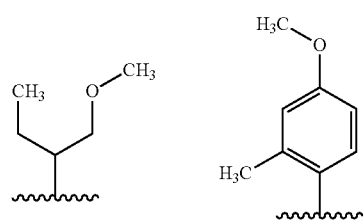

In such embodiments, $R_3$ can be one of

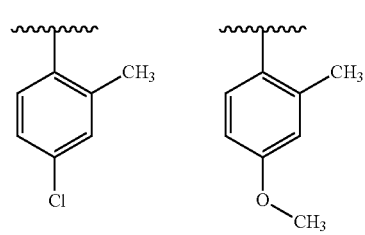

and preferably

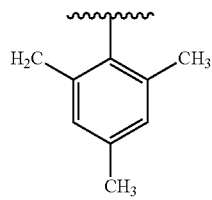

and most preferably

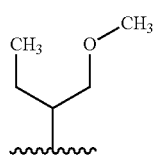

In especially preferred embodiments having compounds of Formula I where $R_2$ is $CH_3$, $R_1$ is

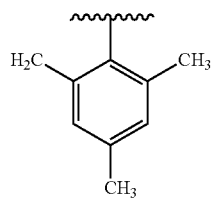

and $R_3$ is

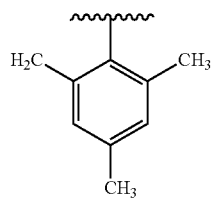

In preferred embodiments, compounds of the inventive subject matter, or pharmaceutically suitable salts thereof, will have a structure according to any one of Formulae II-VIII:

Formula (II)

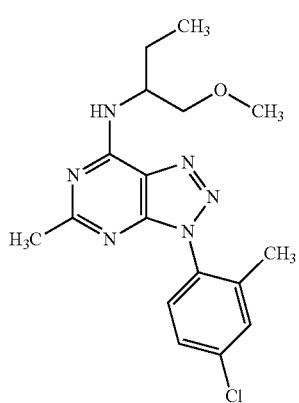

Formula (III)

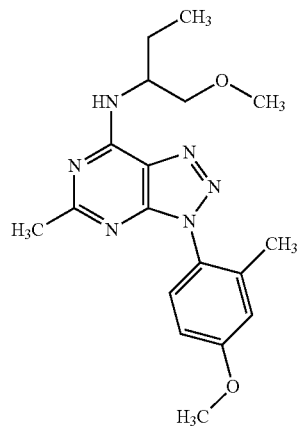

Formula (IV)

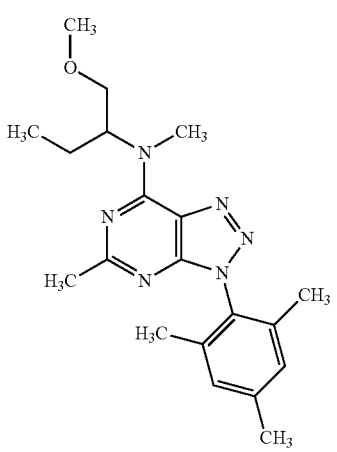

Formula (V)

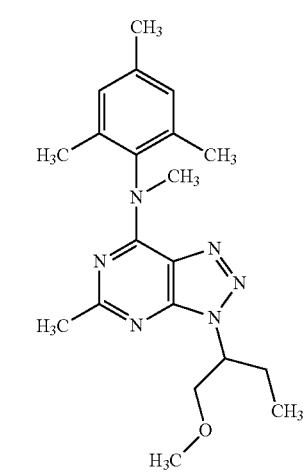

Formula (VI)

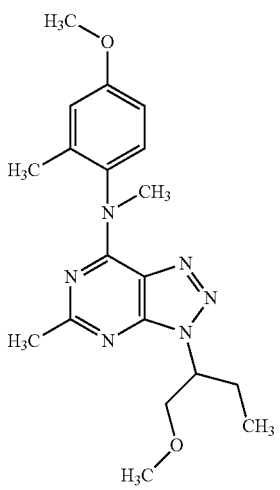

Formula (VII)

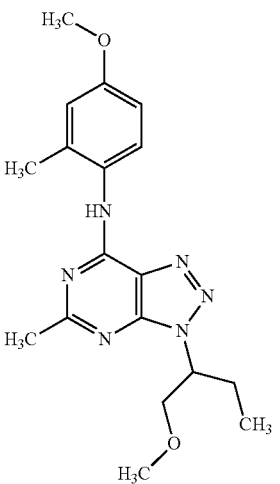

Formula (VIII)

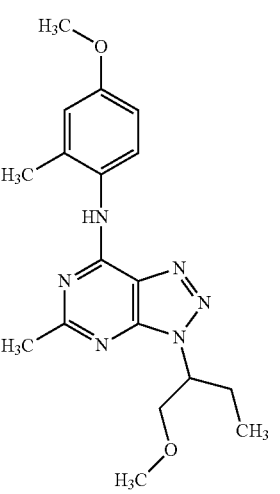

In the most preferred embodiments, compounds of the inventive subject matter, or pharmaceutically suitable salts thereof, will have a structure according to any one of Formulae IV or VII.

While the above structures are shown with specific aryl and heteroaryl groups, numerous suitable alternative aryl or heteroaryl groups include (optionally substituted) aromatic monocyclic or polycyclic groups, typically comprising between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl. Suitable heteroaryl groups will typically include aromatic monocyclic or polycyclic groups comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present inventive subject matter, alkyl groups are substituted with, for example, amino, heterocycloalkyl, such as morpholine, piperazine, piperidine, azetidine, hydroxyl, methoxy, or heteroaryl groups such as pyrrolidine, The term "cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —CO2H, —C(=O)H, CO2-alkyl, —C(=O)alkyl, keto, =N—OH, =N—O-alkyl, aryl, heteroaryl, heterocyclo, —NR'R", —C(=O)NR'R", —CO2NR'R", —C(=O) NR'R", —NR'CO2R", —NR'C(=O)R", —SO2NR'R", and —NR'SO2R", wherein each of R' and R" are independently hydrogen, alkyl, substituted alkyl, or cycloalkyl, or where R' and R" together form a heterocyclo or heteroaryl ring.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "aryl", alone or as part of another group, refers to monocyclic or bicyclic aromatic rings, e.g., phenyl, substituted phenyl and the like, as well as aromatic ring systems where rings are fused, e.g., napthyl, phenanthrenyl and the like. An aryl group may thus contain at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, halogen, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "aromatic" refers to a cyclically conjugated molecular entity with a stability, due to delocalization, significantly greater than that of a hypothetical localized structure, such as the Kekule structure.

The term "heteroatom" refers to any atom other than carbon, for example, N, O, or S.

The term "heteroaryl" herein refers to an aromatic carbocyclic radical in which at least one ring atom is a heteroatom independently selected from nitrogen, oxygen, and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include 5-10-membered rings or 5-6-membered rings, or monocyclic aromatic 5-, 6- and 7-membered rings containing one or more heteroatoms independently selected from nitrogen, oxygen, and sulfur. In another embodiment, exemplary heteroaryl groups include fused ring systems of up to 10, or in another example 9, carbon atoms wherein at least one aromatic ring contains one or more heteroatoms independently selected from nitrogen, oxygen, and sulfur. "Heteroaryl" includes heteroaryl groups fused with an aryl, cycloalkyl, or other heterocyclyl group. Examples of heteroaryl groups include pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, pyrrolopyrimidinyl, pyrazolopyrimidinyl and furopyridinyl.

The term "heterocycle" or "heterocycloalkyl", alone or as part of another group, refers to a cycloalkyl group (non-aromatic) in which one of the carbon atoms in the ring is replaced by a heteroatom selected from O, S and N. The "heterocycle" may have from 1 to 3 fused, pendant, or spiro rings, at least one of which is a heterocyclic ring (i.e., one or more ring atoms is a heteroatom, with the remaining ring atoms being carbon). The heterocyclic ring may be optionally substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy), and aryl (preferably phenyl), the aryl being optionally substituted by halo, lower alkyl and lower alkoxy groups. A heterocyclic group may generally be linked via any ring or substituent atom, provided that a stable compound results.

Typically, a heterocyclic ring comprises 1-4 heteroatoms. Within certain embodiments, each heterocyclic ring has 1 or 2 heteroatoms per ring. Each heterocyclic ring generally contains from 3 to 8 ring members, and heterocycles comprising fused, pendant or spiro rings typically contain from 9 to 14 ring members comprising carbon atoms and one, two, or three heteroatoms selected from nitrogen, oxygen, and sulfur. Therefore, examples of "heterocycle" or "heterocycloalkyl" groups include piperazine, piperidine, morpholine, thiomorpholine, pyrrolidine, imidazolidine, and thiazolide.

In general, the various moieties or functional groups for variables in the formulae may be substituted by one or more suitable "substituents". The term "substituent" as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. Most typically, the substituent will replace a hydrogen.

The term "optionally substituted" means that a group may be substituted at one or more substitutable positions with one or more substituent. For example, suitable optional substituents include alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy), and aryl (preferably phenyl), the aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

All substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like. The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., reduction of tumor cell growth, induction of apoptosis, reduction of metastasis, etc.

The terms "administration of a compound" or "administering a compound" refer to the act of providing a compound according to the inventive subject matter or pharmaceutical composition to the subject in need of treatment.

The term "pharmaceutically acceptable" refers to the fact that the carrier, diluent or excipient must be compatible with the other ingredients of the formulation and not deleterious to the recipient thereof.

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC— $(CH_2)_n$—COOH where n is 0-4, and the like. Similarly, pharmaceutically acceptable cations include sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of non-aqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present inventive subject matter.

Also provided herein are prodrugs of the compounds of Formula I. The term "prodrug" as used herein refers to a modification of contemplated compounds, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

Therefore, the compound described herein can be the compound of Formula I, a pharmaceutically-acceptable salt thereof, a hydrate thereof, a solvate thereof, a tautomer thereof, an optical isomer thereof, E-isomer thereof, Z-isomer thereof, or a combination thereof.

It is contemplated by the inventive subject matter that a compound of Formula I can further comprise or be used in combination with other therapeutic agents or approaches used to treat or prevent AD symptoms. Such therapeutic agents or approaches include disulfiram, honokiol, nimetazepam, tropinol-esters, a TrkA kinase inhibitor, hydantoins, a D2 receptor agonist, an alphal-adrenergic receptor antagonist, an APP-specific BACE Inhibitor, galangin, a galangin prodrug, rutin, a rutin prodrug, an acetylcholinesterase inhibitor, (−)phenserine, enantiomer, tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil, ungeremine, a NMDA receptor antagonist, Memantine, a muscarinic receptor agonist, Talsaclidine, AF-102B, AF-267B (NGX-267), a nicotinic receptor agonist, Ispronicline (AZD-3480), a betasecretase inhibitor, thiazolidinediones, rosiglitazone, pioglitazone, a gamma-secretase inhibitor, semagacestat (LY-450139), MK-0752, E-2012, BMS-708163, PF-3084014, begacestat (GSI-953), NIC5-15, an inhibitor of Aβ aggregation, Clioquinol (PBTI), PBT2, tramiprosate (homotaurine), Scylla-inositol, an Aβ fragment, Bapineuzemab, Epigallocatechin-3-gallate, an anti-inflammatory agent, a cyclooxygenase II inhibitor, an anti-oxidant, Vitamin E, or a ginkolide.

It should be appreciated that in some embodiments pharmaceutical compositions of the inventive subject matter include a pharmaceutically acceptable carrier in combination with a compound as described herein, optionally present as a pharmaceutically acceptable salt, a hydrate, a solvate, or in crystalline form.

In further embodiments, pharmaceutical compositions include compounds of the inventive subject matter in an amount effective to reduce corticotrophin-releasing factor (CRF-1) induced tau protein phosphorylation (p-tau).

Further uses of a compound of the inventive subject matter include use in the manufacture of a pharmaceutical composition, use to reduce CRF-1 activity, use to prevent or delay onset of a pre-Alzheimer's condition or cognitive dysfunction, or use to treat a symptom of Alzheimer's disease.

The inventive subject matter further contemplates a method for treating and/or preventing a symptom of Alzheimer's disease by administering to a subject an effective amount of a compound or pharmaceutical composition as disclosed herein.

Yet further, a method of decreasing, inhibiting, or preventing an increase in p-tau in a mammal is contemplated including administering to the mammal an effective amount of one or more compounds or pharmaceutical compositions of the inventive subject matter.

Experimental Data and Results

Novel compounds that inhibit corticotropin-releasing factor CRF-1 associated phosphorylation of tau are identified herein. Without being bound to a particular theory, it is believed these compounds show efficacy in the treatment of ongoing Alzheimer's Disease, in the delay or prevention of the onset of Alzheimer's disease, in the onset of mild cognitive impairment (MCI) when mediated by an amyloidogenic process, in the delay of a transition from MCI to AD, and in the delay or prevention of MCI.

In people diagnosed with Alzheimer's disease (AD), and in our hands using the 120 mouse model of AD, the level of tau phosphorylation provides the closest 5 correlation to degree of cognitive impairment. The reversal of tau pathology alone can improve memory, even in the presence of high Aβ42 in J20 mice. Stress and the associated increase in corticotropin-releasing factor CRF-1 is known to increase the phosphorylation of tau.

To identify therapeutic candidates, a clinical library of CRF-1 inhibitors to was screened to determine their effects on cortisol-induced p-tau increases. One compound, designated "J03" (N-(4-Methoxy-2-methylphenyl)-1-[1-(methoxymethyl)propyl]-6-methyl-1H-1,2,3-triazolo[4,5-c]pyridine-4-amine) acted as a CRF-1 antagonist (Ki~7.9 nM) and showed no binding to CRFR2 (Ki>10,000 nM). J03 was shown specifically to inhibit stress-induced p-tau increases by cortisol in vitro. Notably, testing of another set of CRF-1 antagonists did not induce a similar inhibition of p-tau.

Following the observations of J03 a number of analogs were developed. One design focus was to replace the triazolopyridine ring of J03 with a triazolopyrimidine ring (see, e.g., FIG. 1) and to explore the orientation of and vary the substituents around the triazolopyridine and triazolopyrimidine rings. It is noted that with respect to any triazolopyridine and triazolopyrimidine described herein a compound with substituents A and B in reversed positions (see, e.g., FIG. 1) is also contemplated. Synthetic schemes have been developed and the analog synthesis has been performed. Biological activity and pharmacokinetics has been evaluated (see, Example 2).

A number of the disclosed compounds are effective in lowering p-tau and/or reducing or preventing a stress-induced increase in p-tau. Moreover, as indicated above, reduction in p-tau (or inhibition of p-tau increase) is an important metric of efficacy in pathologies characterized by the accumulation of amyloid plaque (e.g., Alzheimer's disease, MCI, etc.). It is believed these compounds and analogs thereof, pharmaceutically acceptable salts and clathrates thereof, and the like are useful in the prophylaxis and/or treatment of pathologies characterized by the accumulation of amyloid plaque.

Accordingly it is believed that these agents) (e.g., triazolopyrimidine and/or triazolopyridine compounds described herein, or a tautomer(s) or stereoisomer(s) thereof, or pharmaceutically acceptable salts or solvates of said compounds(s), said stereoisomer(s), or said tautomer(s), or analogues, derivatives, or prodrugs thereof) can be used to decrease p-tau in a mammal, and/or to inhibit or prevent an increase in p-tau, and/or to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by the nonamyloidogenic pathway. In certain embodiments these agents can be used in the treatment of Alzheimer's disease (e.g., to lessen the severity of the disease, and/or to ameliorate one or more symptoms of the disease, and/or to slow the progression of the disease).

Synthetic Protocols:

Contemplated compounds can be prepared using various methods known in the art, and all of those are deemed suitable for use herein. Methods of preparing triazolopyrimidine(s) and/or triazolopyridine(s) such as are described herein are known to those of skill in the art.

Figure 7:
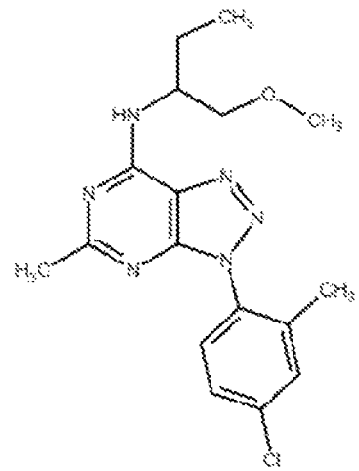
FIG. 7 is the structure for J19.

Generally, in one approach, the relevant triazolopyrimidine and/or triazolopyridine is illustrated in Example 1, below, describing the synthesis of J19 (depicted in FIG. 7). As illustrated therein, the synthesis of J19 involves the preparation of 6-Chloro-N4-substituted pyrimidine-4,5-diamine followed by a cyclisation to the triazolopyrimidine and displacement of the chlorine on the pyrimidine ring to yield the desired analog. A similar synthetic pathway would be used for the other analogs described herein. Additionally, a similar synthetic pathway would be used for the triazolopyridine series, the final product would involve separation of the pyridine isomers.

Figure 2:
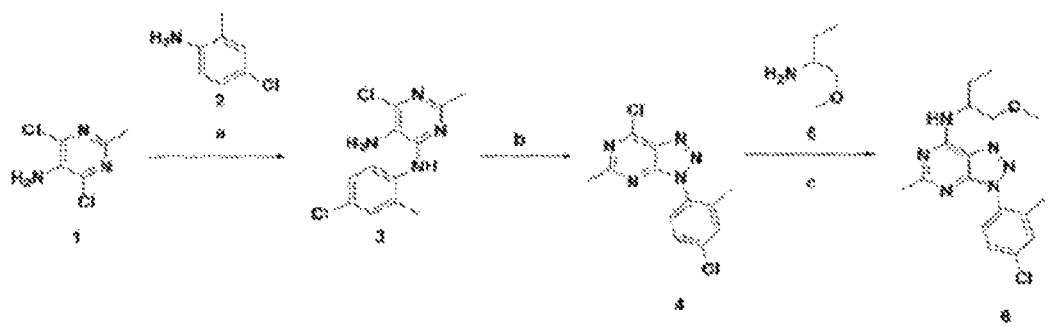
FIG. 2 is a synthesis scheme for J19.

One illustrative, but non-limiting, protocol for the synthesis of J19 is provided in FIG. 2 and Example 1. Synthesis of additional compounds described herein are straightforward variations of the synthesis schemes provided herein.

Contemplated Formulations

The inventive subject matter is also drawn to therapeutic compositions comprising one or more of contemplated compounds as active ingredient in further combination with a pharmaceutically-acceptable carrier. Most typically, such compositions are formulated for administration to a mammalian subject using any suitable route.

The amount of therapeutically active compound that is administered and the dosage regimen for treating a disease condition with the compounds and/or compositions of this inventive subject matter depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

As already noted above, contemplated compounds may be provided as substantially pure compound or as a salt thereof, and pharmaceutically acceptable salts of the compounds include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the inventive subject matter and their pharmaceutically acceptable acid addition salts.

Salts derived from appropriate bases include alkali metal (e.g., sodium and potassium), alkaline earth metal (e.g., magnesium), ammonium and N+($C_{1-4}$ alkyl)$_4$ salts. This inventive subject matter also envisions the quaternization of any basic nitrogen-containing groups of the compounds disclosed herein. Water or oil-soluble or dispersible products may be obtained by such quaternization.

Contemplated compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

For example, contemplated pharmaceutically acceptable compositions may be orally administered in any orally acceptable dosage form including capsules, tablets, troches, elixirs, suspensions, syrups, wafers, chewing gums, aqueous suspensions or solutions. Oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarily pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration or irradiation (e.g., gamma or e-beam), may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Alternatively, the pharmaceutically acceptable compositions of this inventive subject matter may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this inventive subject matter may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this inventive subject matter include mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this inventive subject matter may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this inventive subject matter are formulated for oral administration.

When other therapeutic agents are employed in combination with the compounds of the present inventive subject matter, they may be used for example in amounts as noted in the Physician Desk Reference (PDR) or as otherwise determined by one having ordinary skill in the art.

EXAMPLES

The following examples are provided to further illustrate the present inventive subject matter but, of course, should not be construed as in any way limiting its scope.

Example 1—Synthesis of J19

An illustrative, but non-limiting synthesis scheme for J19 is shown in FIG. 2. Reagents and conditions for synthesis Scheme 1 were: (a) 2-methoxyethanol, 125° C.; (b) NaNO2, DCM, acetic acid, r.t; (c) THF, 100° C., sealed tube.

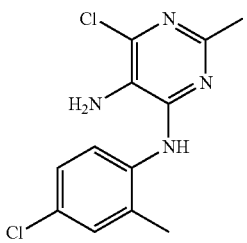 [SMILES: Cc1nc(Cl)c(N)c(Nc2ccc(Cl)cc2C)n1]

6-Chloro-N4-(4-chloro-2-methylphenyl)-2-methylpyrimidine-4,5-diamine (3)

A 250 mL round bottom flask equipped with a reflux condenser was charged with a mixture of 4,6-dichloro-2-methylpyrimidin-5-amine (2.170 g, 12.2 mmol, 1.0 equiv.), 4-chloro-2-methylaniline (1.726 g, 12.2 mmol, 1.0 equiv.) and 2-methoxyethanol (100 mL) and the mixture was heated to an oil bath temperature of 125° C. with stirring under nitrogen. After 48 hours, TLC (1:1 ethyl acetate:hexane) indicated completion of the reaction. The mixture was concentrated under reduced pressure to leave a viscous oil. This was dissolved in ethyl acetate (approximately 30 mL) and the desired product precipitated upon the addition of hexane with stirring (approximately 100 mL). The mixture was allowed to sit at 4° C. overnight and the solid was collected by filtration, washed with hexane and dried under vacuum to give the product as a tan solid (2.4 g, 69%). 1H NMR (CDCl$_3$, 300 MHz): δ 7.81 (d, J=9.3 Hz, 1H), 7.21-7.19 (m, 2H), 6.79 (bs, 1H), 3.29 (bs, 2H), 2.49 (s, 3H), 2.29 (s, 3H), LC/MS: 283.3 (M+1).

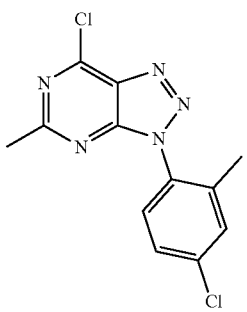

7-Chloro-3-(4-chloro-2-methylphenyl)-5-methy-3H-[1,2,3]triazolo[4,5-d]pyrimidine (4)

Sodium nitrite (0.289 g, 4.2 mmol, 1.1 equiv.) was added to a vigorously stirring mixture of 6-chloro-N4-(4-chloro-2-methylphenyl)-2-methylpyrimidine-4,5-diamine (1.060 g, 3.7 mmol, 1.0 equiv.) in dichloromethane (15 mL) and acetic acid (15 mL) at room temperature. After 45 minutes, TLC indicated complete disappearance of the starting material (1:3 ethyl acetate:hexane). The mixture was transferred to a separatory funnel and 50 mL of water was added. The dichloromethane layer was removed and washed with water, brine and dried over magnesium sulfate. The organic layer was then concentrated to dryness to leave a tan solid which was used directly without further purification (1.10 g, 100%). 1H NMR (CDCl$_3$, 300 MHz): 7.46-7.35 (m, 3H), 2.85 (s, 3H), 2.19 (s, 3H). LC/MS: 294.2 (M)$^+$.

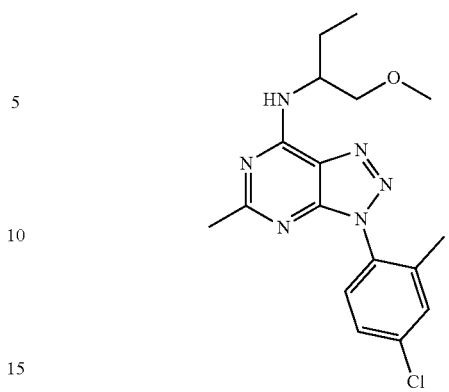

3-(4-Chloro-2-methylphenyl)-N-(1-methoxybutan-2-yl)-5-methyl-3H-[1,2,3]triazolo[4,5-d]pyrimidin-7-amine (6)

A mixture of 7-chloro-3-(4-chloro-2-methylphenyl)-5-methyl-3H-[1,2,3]triazolo[4,5-d]pyrimidine (1.0 g, 3.4 mmol, 1.0 equiv.) and 1-methoxybutan-2-amine (0.89 g, 8.9 mmol, 2.5 equiv.) in THF (15 mL) was heated in a sealed reaction vessel to an oil bath temperature of 100° C. with stirring. After 3 hours, TLC (20% ethyl acetate in hexanes) indicated complete disappearance of starting material and formation of a single product. The mixture was allowed to cool to room temperature. The mixture was concentrated to dryness and purified by flash chromatography over silica gel (0 to 100% ethyl acetate/hexane gradient) to give the title product as a white solid after drying. (0.47 g, 60.8%). $^1$H NMR (CD3OD, 300 MHz): δ7.54-7.53 (m, 1H), 7.46-7.38 (m, 2H), 4.69-4.59 (in, 1H), 3.63-3.50 (m, 2H), 3.40 (s, 3H), 2.49 (s, 3H), 2.12 (s, 3H), 1.90-1.62 (m, 2H), 1.02 (t, 7.5 Hz, 3H). $^{13}$C-NMR (75 MHz, CD3OD) δ 9.89, 16.87, 24.45, 24.99, 25.09, 51.60, 55.06, 58.17, 74.04, 74.53, 126.96, 128.98, 131.00, 132.83, 135.97, 137.80, 150.12, 10 155.01, 168.03. LC-MS (m/z): 360 [M]+, 362 [M+2]+.

Example 2—Evaluation of J03 and Analogs

As described below, in vitro studies were performed using SHSY-5Y cells. These cells are a useful neurological model that differentiate into cells with morphological and biochemical characteristics of mature neurons including mature isoforms of tau.

Animal experiments were performed using J20 mice. The J20 mouse is a model of for Alzheimer's disease. This model overexpresses human APP with two mutations linked to familial Alzheimer's disease (the APP KM670/671NL (Swedish) and 5APP V717F (Indiana) mutations).

Figures 3, 4, 5:
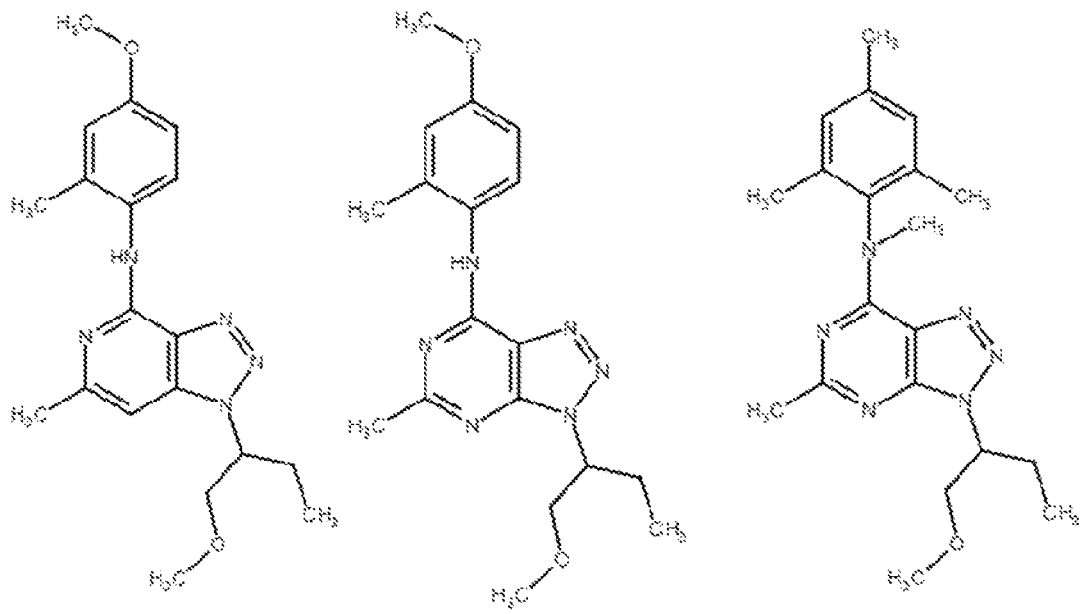
FIG. 3 is the structure for J03.
FIG. 4 is the structure for J04.
FIG. 5 is the structure for J14.
Figure 6:
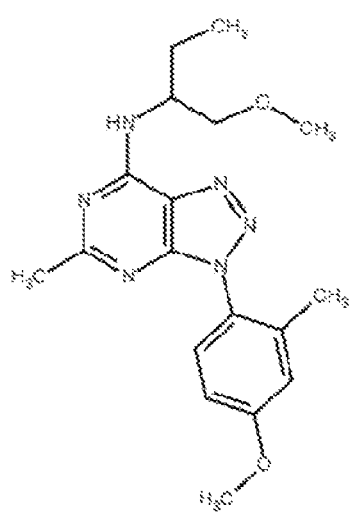
FIG. 6 is the structure for J17.
Figure 8:
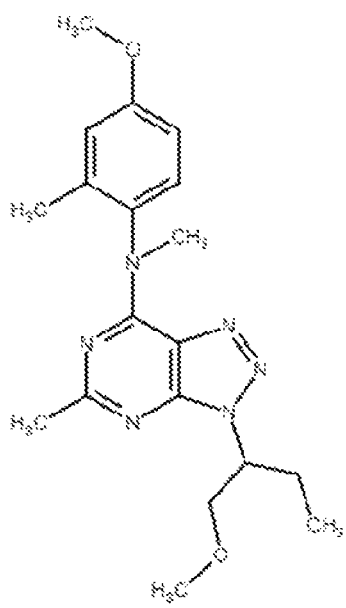
FIG. 8 is the structure for J30.
Figure 9:
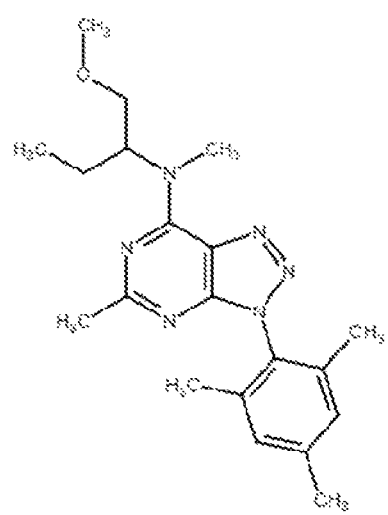
FIG. 9 is the structure for J32.

The effects of J03 (FIG. 3) and analogs J04 (FIG. 4), J14 (FIG. 5), J17 (FIG. 6), J19 (FIG. 7), J30 (FIG. 8), and J32 (FIG. 9) on tau and p-tau levels were studied.

Figure 10A:
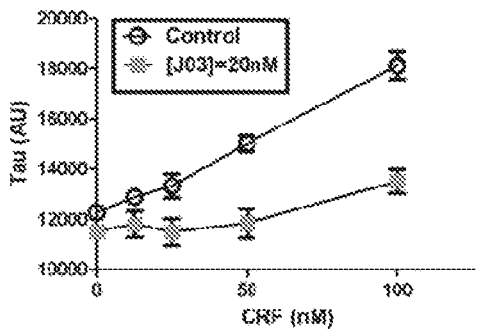
FIGS. 10A-10I reflect experimental results for studies with J03.
Figure 10B:
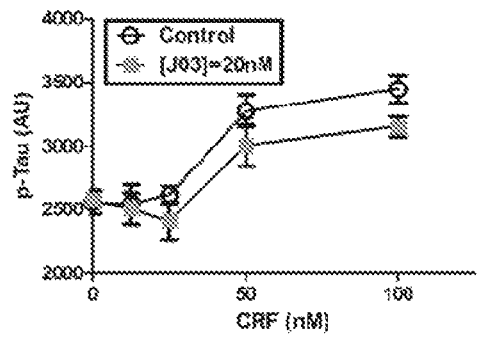

As shown in FIGS. 10A and 10B, J03 reduces tau and phospho-tau (p-tau) increases induced by CRF. In an initial study, SHSY-5Y cells were cultured without serum to induce differentiation and increase tau expression. CRF was added to the cultures at increasing concentrations and, as shown in FIGS. 10A and 10B, both tau (FIG. 10A) and phospho-tau (FIG. 10B) increased with CRF in a dose-dependent manner. The increases were proportional and both were about 50%. J03 reduced the CRF-induced tau increases more than the p-tau increases. The increase in tau was unpredictable as CRF reduces neuronal differentiation (see Chen et al. (2004) Proc. Natl. Acad. Sci. USA, 101(44): 15782-15787), however, it can increase tau accumulation.

Figure 10C:
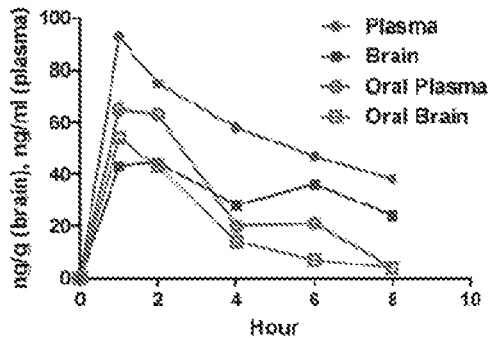

A standard pharmacokinetic study of J03 was performed in which J03 (10 mk delivered in a 5 mg/ml DMSO stock, 50 ml) was injected subcutaneously (SQ) into J20 mice. As shown in FIG. 10C, J03 brain levels were low and the brain/plasma ratio was 1:2, but levels stayed up for hours, resulting in good exposure of brain tissue, even from a single injection. After oral delivery by feeding (not gavage) also at 10 mg/kg, brain levels were slightly higher at the peak (open grey box), and the brain:plasma ratio was close to 1:1.

Figure 10D:
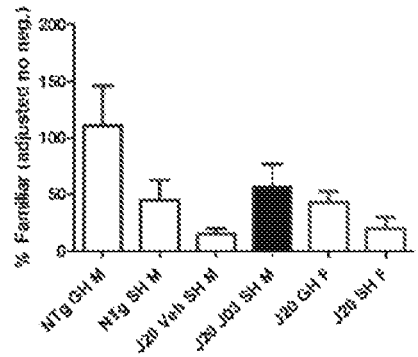
Figure 10E:
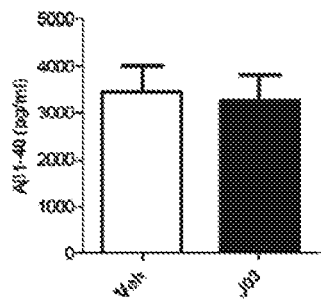
Figure 10F:
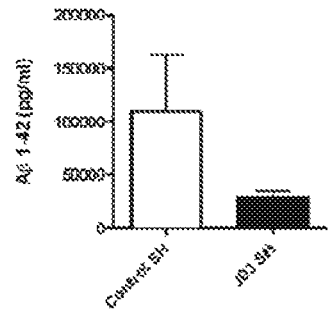
Figure 10G:
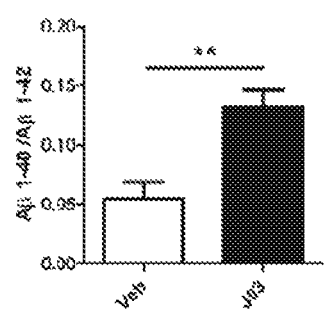
Figure 10H:
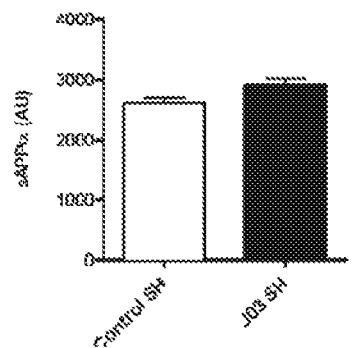
Figure 10I:
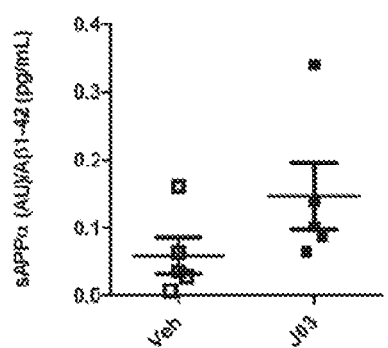

In pilot study #1, J20 mice housed singly were treated by SQ injection of J03 in PEG/b-MCD at 10 mkd for 12 days. NOR analysis of object memory (N=5/group) was performed. The results are illustrated in FIGS. 10D-10I. As shown there was a slight improvement in behavior in single housed J03-treated J20 mice (FIG. 10D). There was no difference in Aβ1-40 (FIG. 10E), but a decrease in Aβ1-42 (FIG. 10F). The Aβ1-40/1-42 ratio was significantly increased (FIG. 10G). SAPP was very slightly increased (FIG. 10H), as was the sAPP/Aβ1-42 ratio (FIG. 10I).

Figure 11A:
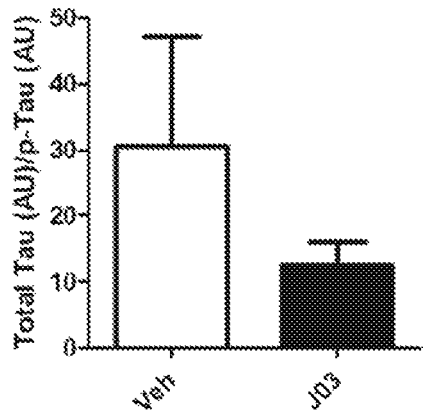
FIGS. 11A-11C reflect experimental results for studies with J03 with respect to tau and p-tau.
Figure 11B:
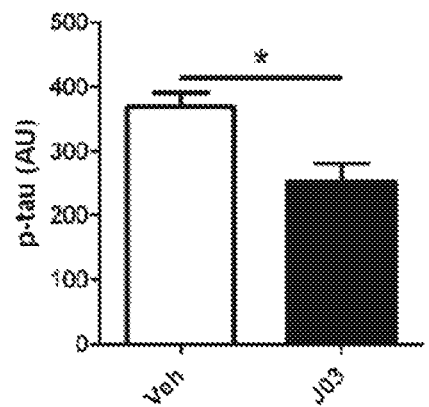
Figure 11C:
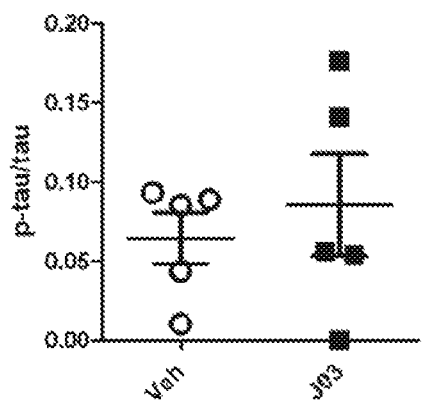

Total tau was decreased by J03 (FIG. 11A), but largely due to one mouse. P-tau was significantly lower (FIG. 11A), and the ratio was slightly higher, but with great individual variation (FIG. 11A).

Based on these promising results, the study was repeated (pilot study #2) with oral delivery and a longer duration.

Figure 12A:
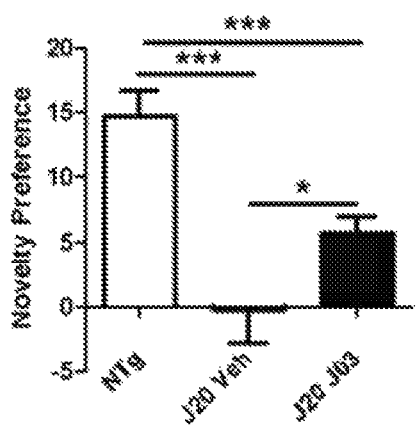
FIGS. 12A-12B reflect experimental results for studies with J03 with respect to memory.
Figure 12B:
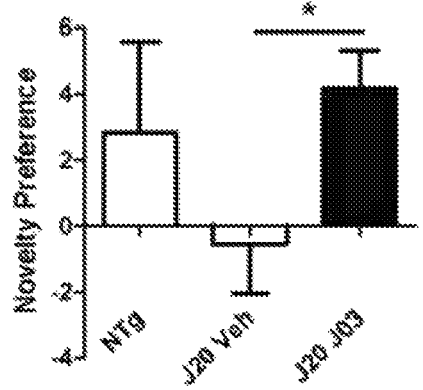

As illustrated in FIGS. 12A and 12B, J03 treated mice performed well in both novel location (FIG. 12A) and novel object (FIG. 12A) assays.

Figure 13A:
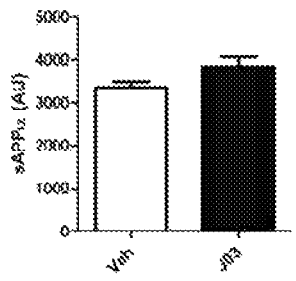
FIGS. 13A-13C reflect experimental results for studies with J03 with respect to sAPPα.
Figure 13B:
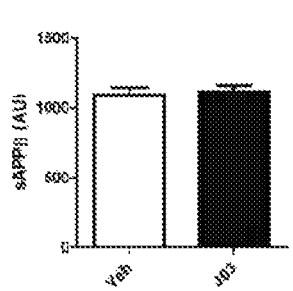
Figure 13C:
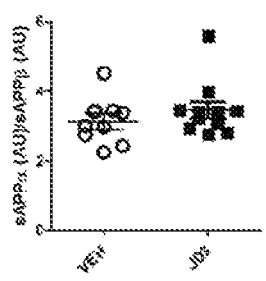
Figure 14A:
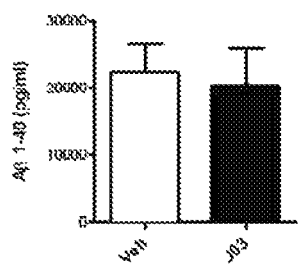
FIGS. 14A-14C reflect experimental results for studies with J03 with respect to Aβ.
Figure 14B:
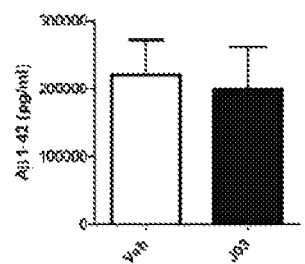
Figure 14C:
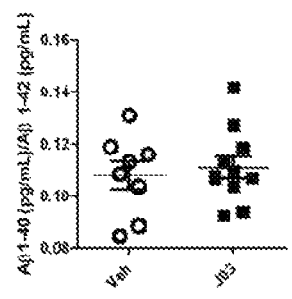

As shown in FIGS. 13A-13C, sAPPα increased slightly (FIG. 13A), sAPPβ was unchanged (FIG. 13B), and the sAPPα/sAPPβ ratio (FIG. 13C) was slightly increased. Both Aβ1-40 (FIG. 14A) and Aβ1-42 (FIG. 14B) were unchanged with no significant trend to increase. The Aβ1-40/Aβ1-42 ratio (FIG. 14C) was unchanged.

Figure 15:
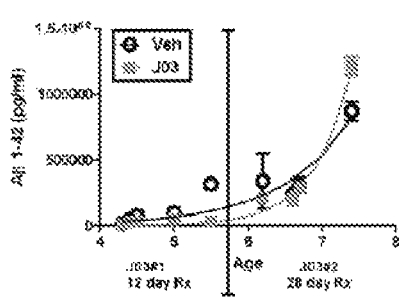
FIG. 15 reflects experimental results for studies with J03 with respect to Aβ.

FIG. 15 illustrates the effects of J03 on Aβ1-42 in pilot studies #1 and #2. The curves here suggest there is some Aβ1-decreasing effect if treatment is started in younger mice, but it is lost if treatment is started after Aβ amplification is underway.

Figure 16:
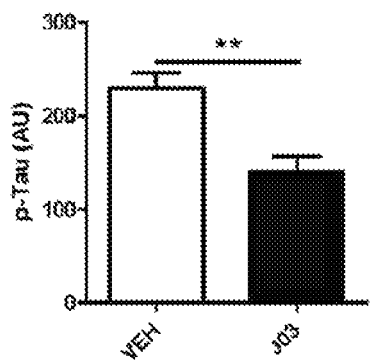
FIG. 16 reflects experimental results for studies with J03 with respect to p-tau.

FIG. 16 shows the effect of J03 on p-tau in pilot study #2. Not only was p-tau decreased again here as it was in pilot study #1, the decrease reached statistical significance.

FIGS. 17A-17F shows the effect of J03 on p-tau and memory. There was good correlation to p-tau levels (FIG. 17B). Mice that scored above 8 had significantly lower p-tau levels (FIG. 17C). Novel location preference was even clearer for J03-treated J20 mice (FIG. 17D), and also showed good correlation to p-tau levels (FIG. 17E), and mice that scored over 0, therefore showing some novel location preference, had significantly lower p-tau (FIG. 17F).

To obtain an early look at plasma and brain J03 levels after oral dosing in formulation, two additional mice were dosed on the first day of the study and euthanized two hours later. In these mice brain levels were higher than expected, at 170 ng/g, (FIG. 18A) but with great variation between the two mice. At the end of the study brain levels were in the expected range of about 35 ng/g (FIG. 18B).

Figure 20A:
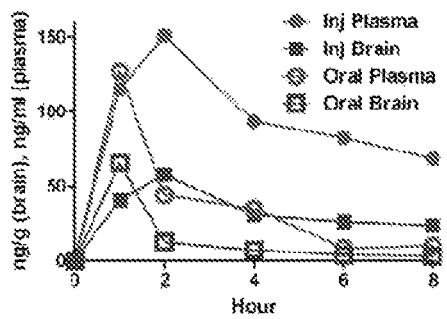
FIGS. 20A-20B reflect experimental results for J04.
Figure 20B:
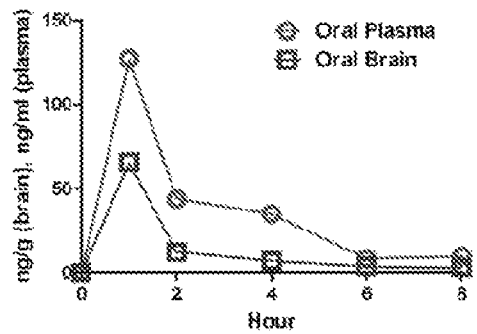

J04 was designed as an analog with replacement of the triazolopyridine with the triazolopyrimidine ring. In a primary screen in SH-Sy5Y cells, J04 did not lower tau in the primary screen, but did lower p-tau (see, FIG. 19). J04 lowered p-tau to the same level as J03. Brain levels after SQ injection or oral delivery (FIG. 20A) were similar at ~55 ng/g, although clearance after injection was slower. Clearance after oral delivery is shown in FIG. 20B.

Figure 21A:
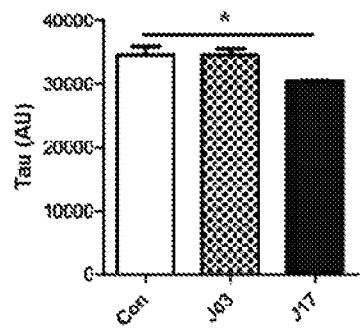
FIGS. 21A-21E reflect experimental results for studies with J17.
Figure 21B:
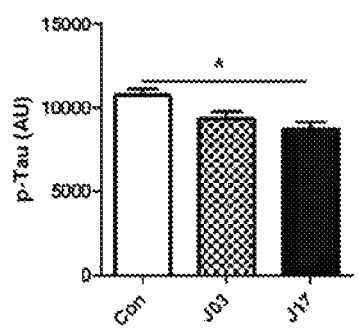

J17 was observed to significantly lower tau (FIG. 21A), and p-tau (FIG. 21B) in SH-Sy5Y cells and the effect was greater than that measured for J03.

Figure 21C:
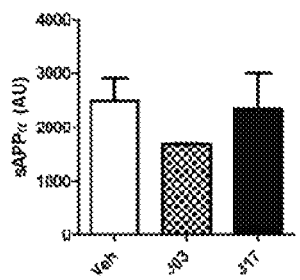
Figure 21D:
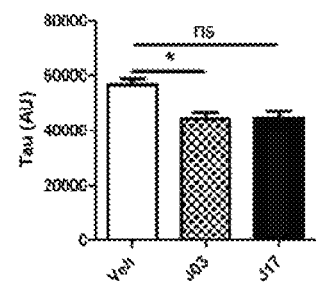
Figure 21E:
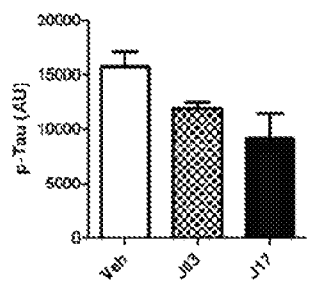

As shown in FIG. 21C, after exposure to CRF, sAPPα was the same for control as for J17, but lower for J03 in this experiment. Tau was decreased for both J03 and J17 (FIG. 21D). P-tau was decreased for both J03 and J17 (FIG. 21E).

Figure 22A:
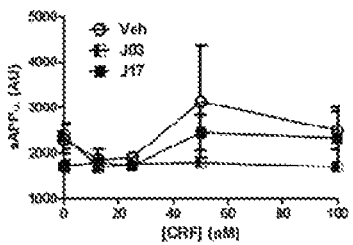
FIGS. 22A-22C reflect further experimental results for studies with J17.
Figure 22B:
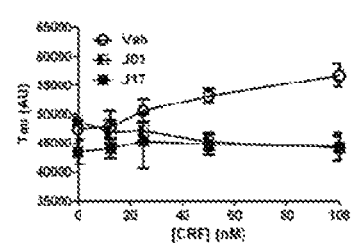
Figure 22C:
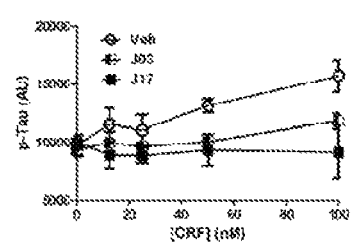

FIGS. 22A-22B illustrate the effect of J03 and J17 on sAPPα, tau, and p-tau with increasing concentrations of CRF. The decrease in sAPPα with J17 was seen without CRF and at 50 nM (FIG. 22A), but not at other concentrations. The decrease in tau was seen without CRF and at 50 and 100 nM (FIG. 22B). The decrease in p-tau was seen at all concentrations of CRF tested, excluding 0 (FIG. 22C).

Figure 23A:
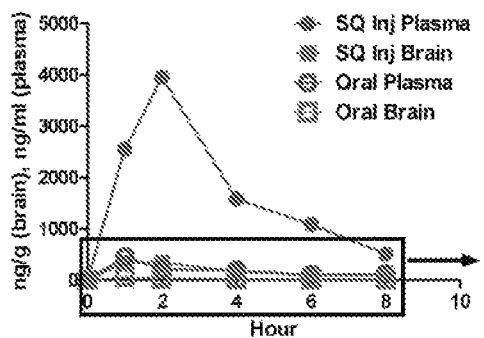
FIGS. 23A-23B reflect yet further experimental results for studies with J17.
Figure 23B:
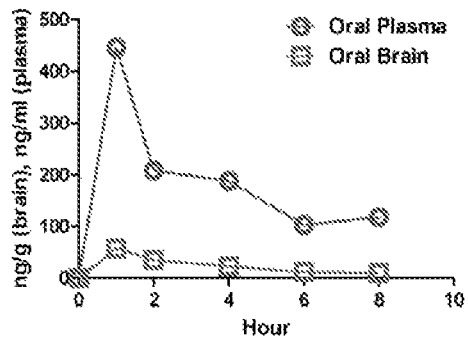

FIGS. 23A-23B illustrate in vivo pharmacokinetics of J17. After subcutaneous injection of 10 mg/kg, brain levels were low (~400 ng/g) relative to plasma levels (~4000 ng/m) (FIG. 23A). After oral delivery at the same dose, brain levels were only ~50 ng/g and plasma levels were once again almost 10-fold higher (FIG. 23B).

Figure 24A:
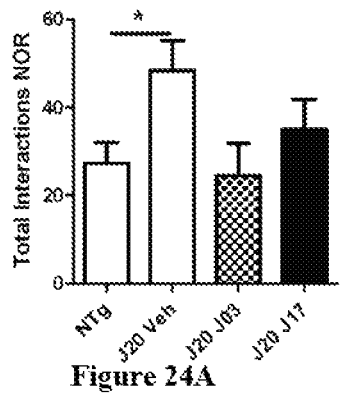
FIGS. 24A-24D reflect still further experimental results for studies with J17.
Figures 24B, 24C, 24D:
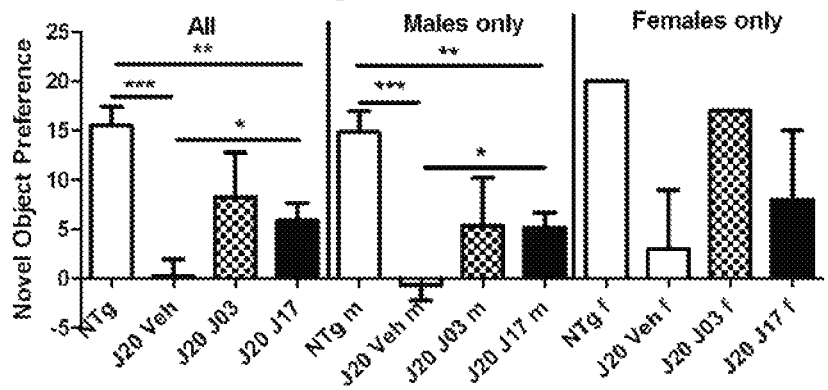

In a J17 pilot study (#1 pilot study) male and female J20 mice were housed singly and treated with J17 at 10 mkd by oral delivery for 28 days. The results for males and females showed some differences and are presented together and separately in FIGS. 24A-24D. As shown therein, both J03 and J17 lowered activity, but not significantly due to individual variation (FIG. 24A). Overall, J03 increased novel object preference more than 17, but only the increase with J17 was significant as there was less variation (FIG. 24B). Males (n=6 per group) showed a pattern similar to all the mice (FIG. 24C), with the improvement in memory being less and more similar between J03 and J17.

Figure 25A:
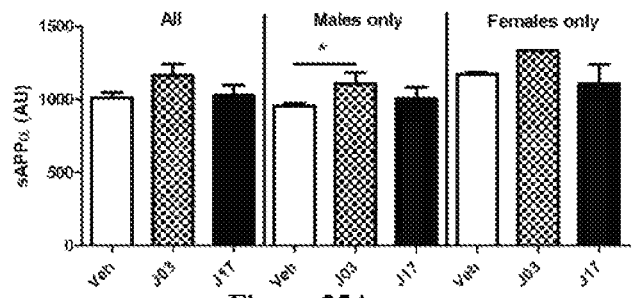
FIGS. 25A-25C reflect additional experimental results for studies with J17.
Figure 25B:
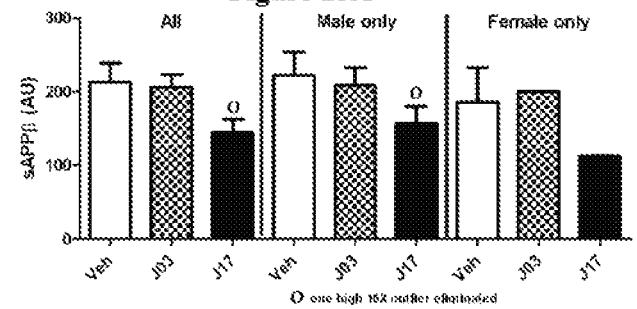
Figure 25C:
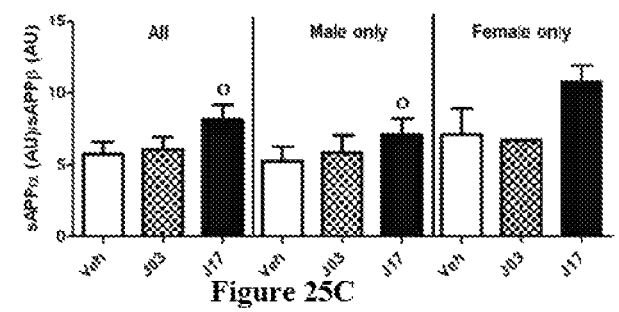

FIGS. 25A-25C shows the effect of J03 and J17 on sAPPα, sAPPβ, and the ratio sAPPα/sAPPβ. The sAPPα results were similar for both genders and showed an increase with J03 but not J17 (FIG. 25A). sAPPβ results were also similar. There was a decrease with J17 only (FIG. 25B). There was only a slight increase in the ratio for males with J03, and it was greater with J17, but the two females showed an even greater increase in the ratio (FIG. 25C).

Figure 26A:
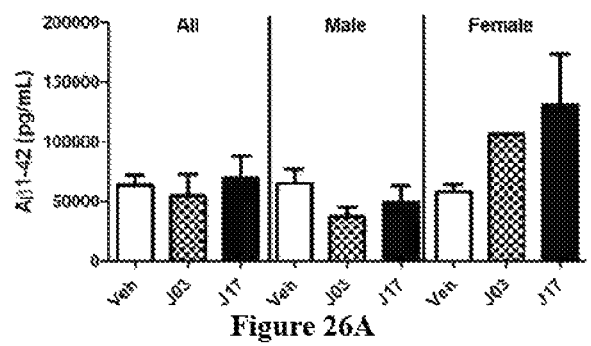
FIGS. 26A-26C reflect more experimental results for studies with J17.
Figure 26B:
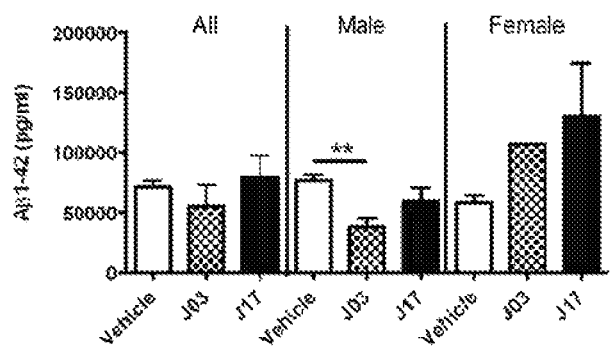
Figure 26C:
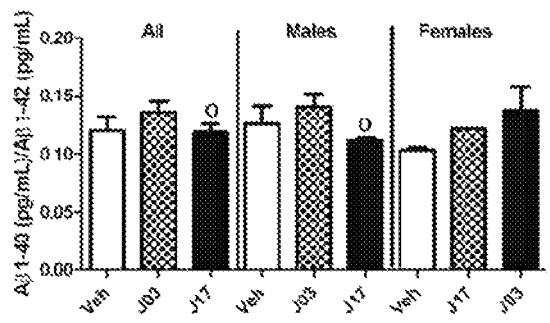

When data from all mice are presented (FIG. 26A), there are no significant differences in Aβ1-42, but when the low outlier (10-fold lower) from one sibling pair was eliminated, there is a significant reduction in Aβ1-42 in male mice (FIG. 26B). There was no significant difference in the Aβ1-40/Aβ1-42 ratio (FIG. 26C).

Figure 27A:
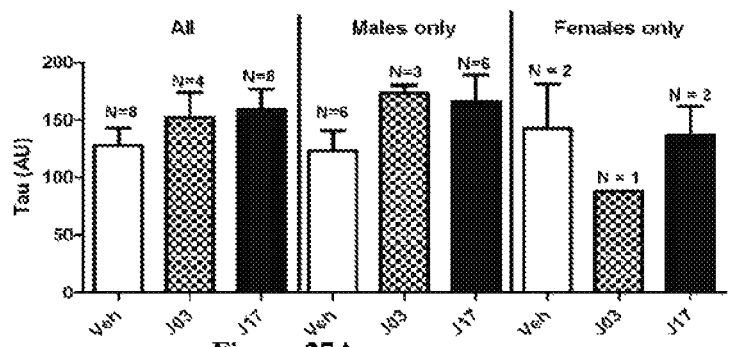
FIGS. 27A-27C reflect still more experimental results for studies with J17.
Figure 27B:
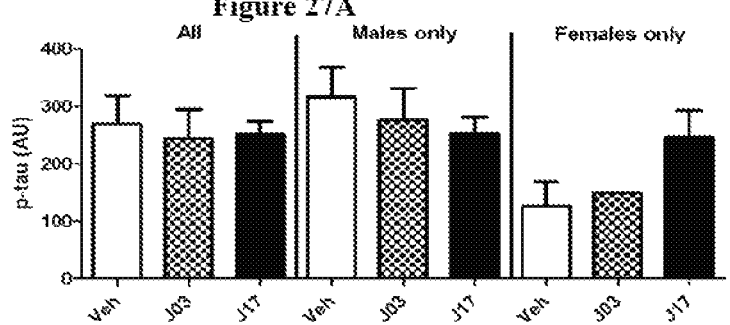
Figure 27C:
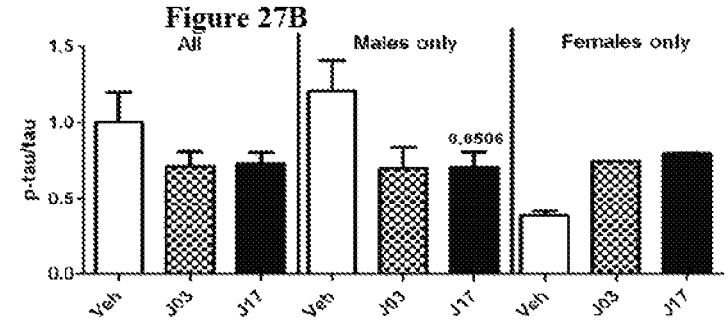

Tau (FIG. 27A) was increased in males, but an important readout for this series of compounds, p-tau, was slightly lower in male mice ((FIG. 27B) and the p-tau/tau ratio ((FIG. 27C) was lower still.

Figure 28A:
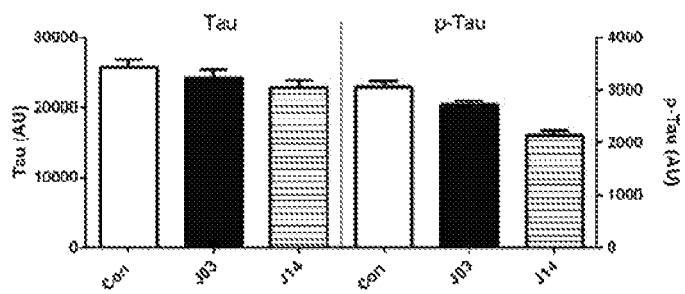
FIGS. 28A-28B reflect experimental results for studies with J14.
Figure 28B:
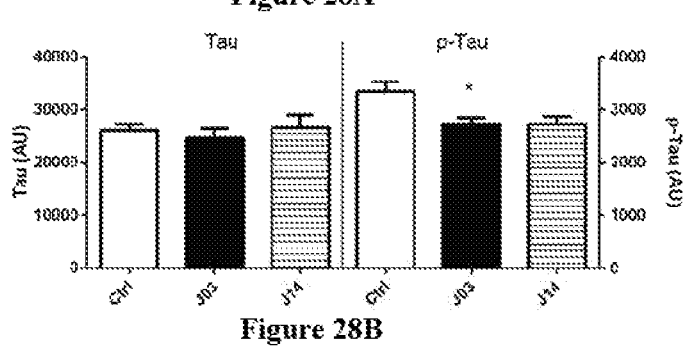

J14 is an analog of J03 and part of the triazolopyrimidine series described herein. FIGS. 28A-28B illustrate two screens for tau and p-tau levels. J14 decreased both total tau and p-tau levels more than J03 in FIG. 28A, while neither J14 nor J03 decreased total tau or p-tau in FIG. 28B.

Figure 29A:
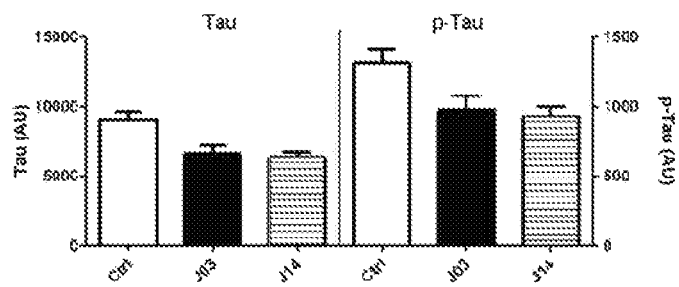
FIGS. 29A-29C reflect further experimental results for studies with J14.

As depicted in FIG. 29A, when screened with CRF-1 at 100 nM for 3 days, both J03 and J14 (at 20 nM) decreased total tau and p-tau.

Figure 29B:
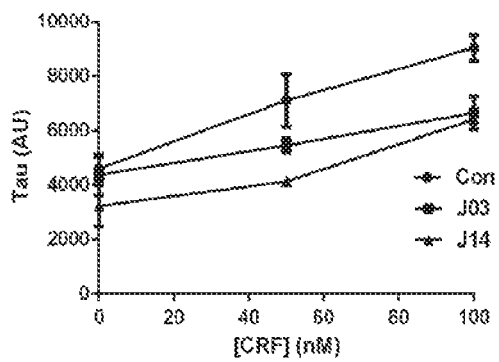
Figure 29C:
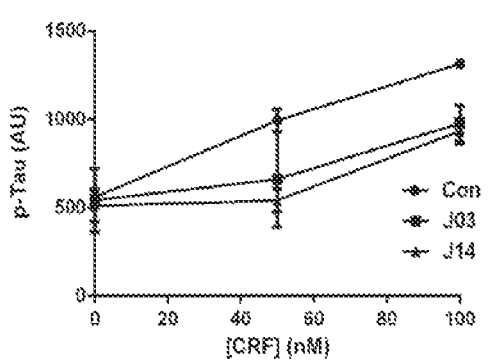

FIGS. 29B-29C depicts screening with CRF-1 at 0 nM, 50 nM, and 100 nM, and shows that total tau and p-tau increase with CRF-1 concentration, with J14 decreasing p-tau and tau more than J03.

After subcutaneous injection at 10 mg/kg, plasma (798 ng/mL) and brain (485 ng/g) levels peaked 2 hours after injection, with a brain:plasma ratio of 0.6, as seen in FIG.

Figure 30A:
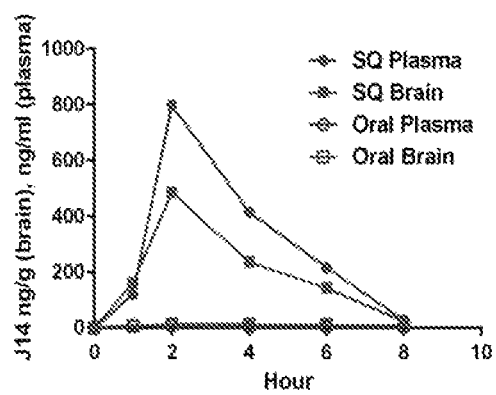
FIGS. 30A-30B reflect yet further experimental results for studies with J14.
Figure 30B:
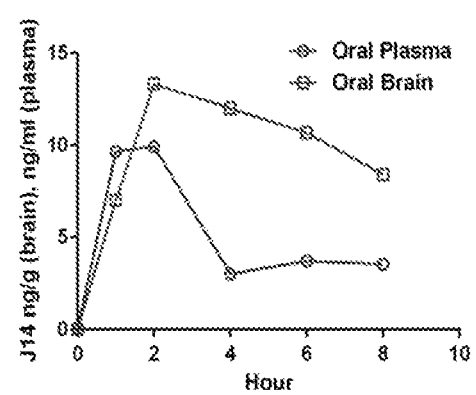

30A. After oral feeding at the same dose of 10 mg/kg, brain levels also peaked at 2 hours, but at a much lower level of 13.3 ng/g (FIG. 30B). The brain:plasma ratio was 1.33.

Figure 31A:
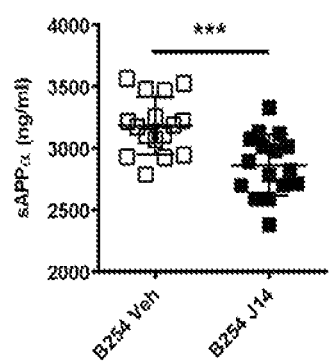
FIGS. 31A-31F reflect still further experimental results for studies with J14.
Figure 31B:
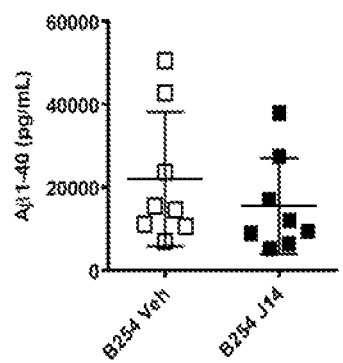
Figure 31C:
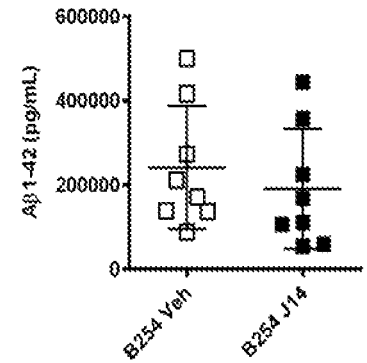
Figure 31D:
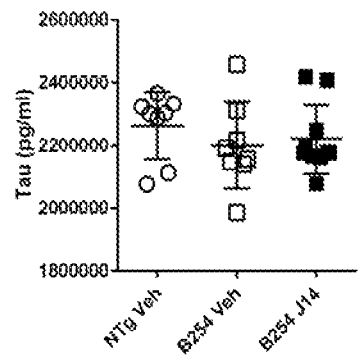
Figure 31E:
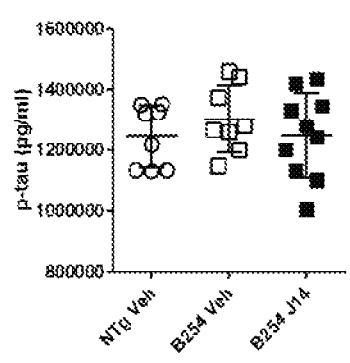
Figure 31F:
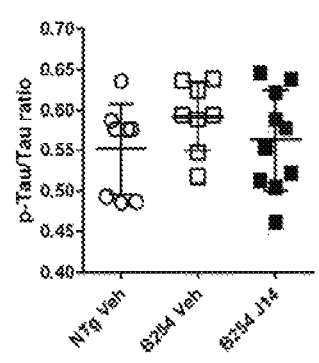

FIGS. 31A-31F depict total sAPPα, Aβ1-40, and Aβ1-42, and tau, p-tau, and p-tau/tau ratio, respectively, after daily SQ injection at 10 mkd does for 12 days. FIG. 31A shows a decrease in sAPPα for J14 treated mice compared to vehicle treated mice. There was a trend toward decrease in both Aβ1-40, and Aβ1-42 (FIGS. 31B-31C). There was a trend for lower levels of tau protein for both vehicle and J14 treated B254 mice having the Swedish and Indiana mutations, but also a D664A APP mutation that prevents caspase cleavage, as seen in FIGS. 31D-31F.

Figure 32A:
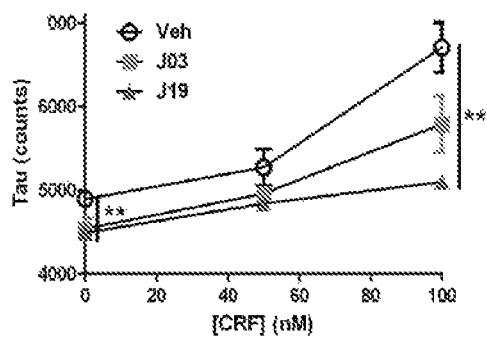
FIGS. 32A-32H reflect experimental results for studies with J19.
Figure 32B:
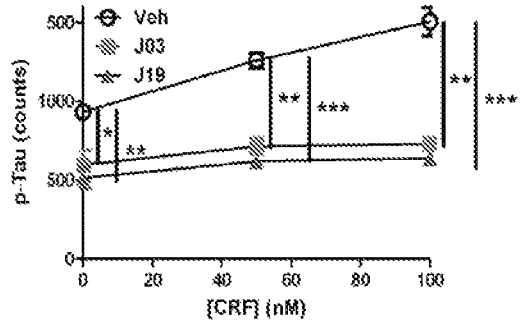
Figure 32C:
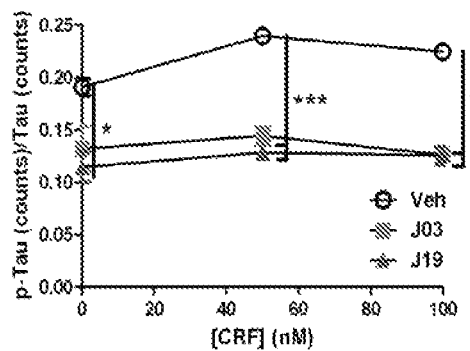
Figure 32D:
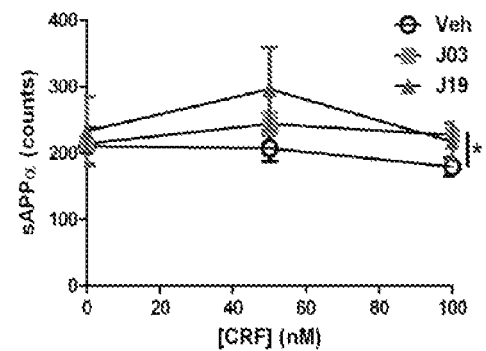
Figure 32E:
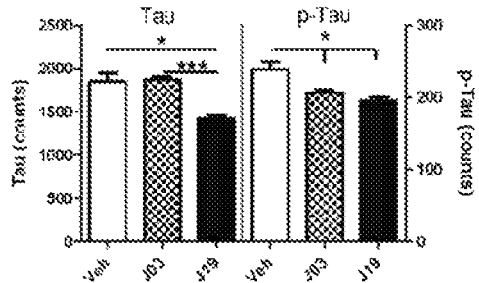
Figure 32F:
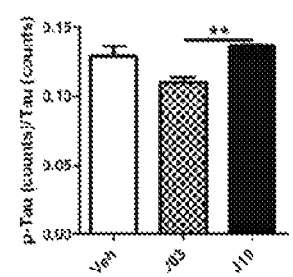

J19 is an analog of J03 similar to J17 and is part of the triazolopyrimidine series described herein. FIGS. 32A-32D illustrate the effect of J03 and JI9 on CRF-induced tau and p-tau alterations. J03 significantly decreased tau both in the absence of CRF and in the presence of 100 nM CRF (FIG. 32A). J19 also showed a trend to decrease tau. Both J03 and J19 significantly reduced p-tau in the presence and absence of CRF (FIG. 32B). The p-tau/tau ratios were highly significantly decreased by J03 and J19 at both 50 and 100 nM CRF, and were decreased in the absence of CRF (FIG. 32C). There was a trend for sAPPα to be higher with J03 and JI9 that reached significance for J03 at 100 nM CRF (FIG. 32D).

JI9 decreased tau and both J03 and JI9 decreased p-tau (FIG. 39E). Therefore, while the p-tau/tau ratio looks unchanged for J19 FIG. 39F. This is due to the tau decrease and not due to a lack of effect.

Figure 32G:
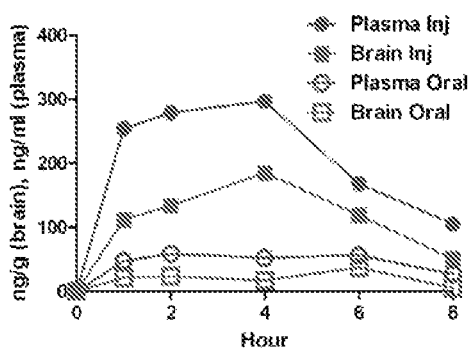
Figure 32H:
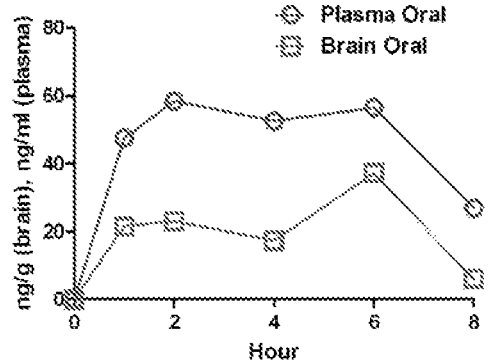

FIGS. 32G-32H illustrate the in vivo pharmacokinetics of J19. After SQ injection of J19 at 10 mkd, brain levels were ~190 ng/g at the peak 4 hours after injection. Levels remained relatively high until 8 hours (left panel). With oral delivery (right panel), levels were much lower, but again remained detectable from 1 to 6 hours.

Figure 33A:
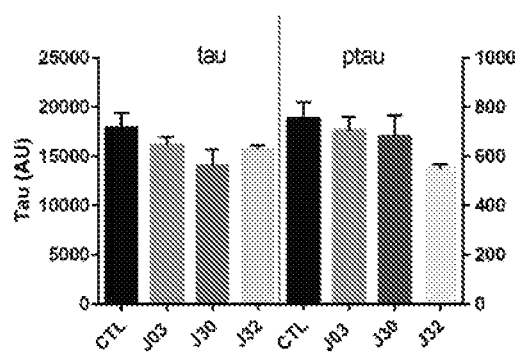
FIGS. 33A-33B reflect experimental results for studies with J30 and J32.
Figure 33B:
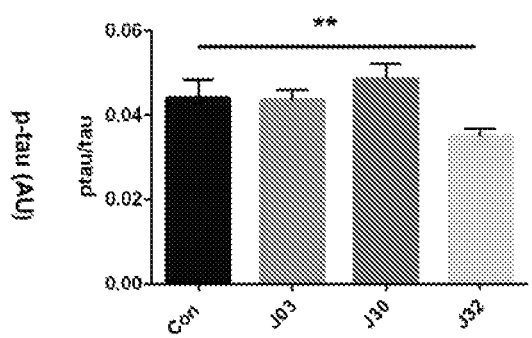

FIGS. 33A-33B depict the p-tau and tau-lowering effects of J30 and J32 compared to a control J03. As depicted, J30 lowered total tau levels, while J32 significantly lowered the p-tau/tau ratio.

Figure 33C:
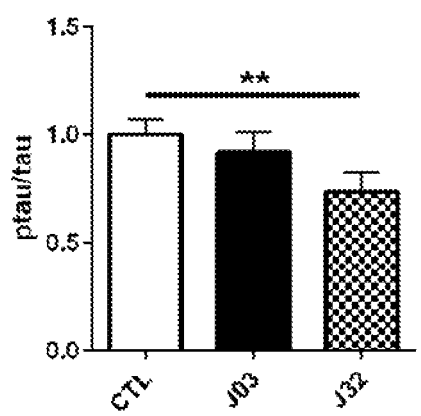
FIGS. 33C-33D reflect experimental results for studies with J32.
Figure 33D:
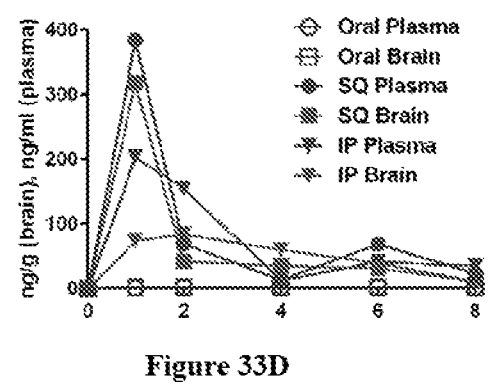

J32 was further studied for its effects on p-tau/tau ratio. FIG. 33C illustrates the significant decrease in p-tau/tau ratio by J32 compared to J03 and a control for 1 µM of J32 in a SH-SY5Y cells. Further, FIG. 33D illustrates favorable concentrations of J32 in the brain and blood serum after SQ injection, intraperitoneal injection (IP), and oral administration of 10 mg/kg doses. Plasma and brain levels peaked 1 hour after SQ injection, with a brain:plasma ratio of 0.75. After IP injection, brain levels peaked at 2 hours but cleared out slowly over 8 hours. Oral dosing at gave much lower levels in plasma and brain.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used in the description herein and throughout the claims that follow, the meaning of "a," "an," and "the" includes plural reference unless the context clearly dictates otherwise. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A compound having Formula II:

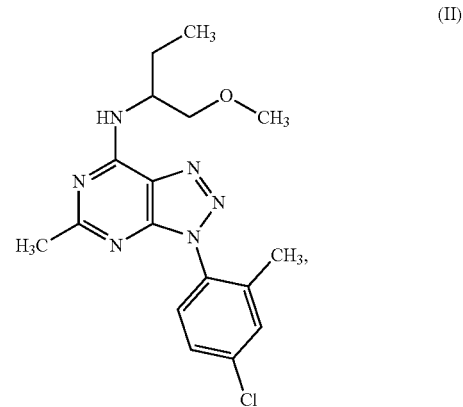 [SMILES: CCC(COC)Nc1nc(C)nc2c1nnn2-c1ccc(Cl)cc1C]

2. A pharmaceutical composition, comprising a pharmaceutically acceptable carrier in combination with a compound according to claim 1.

3. The pharmaceutical composition of claim 2, wherein the compound is present in therapeutically effective amount.

4. The pharmaceutical composition of claim 2, wherein the composition is formulated for oral administration or injection.

* * * * *